(12) United States Patent
Cheng et al.

(10) Patent No.: US 10,155,244 B2
(45) Date of Patent: Dec. 18, 2018

(54) FLUID DEPOSITION APPARTUS AND METHOD

(71) Applicant: Taiwan Semiconductor Manufacturing Co., Ltd., Hsin-Chu (TW)

(72) Inventors: Chun-Wen Cheng, Zhubei (TW); Jung-Huei Peng, Jhubei (TW); Yi-Shao Liu, Zhubei (TW); Fei-Lung Lai, New Taipei (TW); Shang-Ying Tsai, Pingzhen (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 1223 days.

(21) Appl. No.: 14/027,368

(22) Filed: Sep. 16, 2013

(65) Prior Publication Data

US 2015/0079704 A1    Mar. 19, 2015

(51) Int. Cl.
*H01L 21/66* (2006.01)
*B01J 19/00* (2006.01)
(Continued)

(52) U.S. Cl.
CPC ....... *B05C 11/1039* (2013.01); *B01J 19/0046* (2013.01); *B05D 1/18* (2013.01); *B05D 5/04* (2013.01); *G01N 27/4145* (2013.01); *G01R 1/06783* (2013.01); *G01R 31/2886* (2013.01); *G01R 31/2887* (2013.01); *G01R 31/2889* (2013.01); *B01J 2219/0043* (2013.01); *B01J 2219/00286* (2013.01); *B01J 2219/00353* (2013.01); *B01J 2219/00387* (2013.01); *B01J 2219/00418* (2013.01); *B01J 2219/00596* (2013.01); *B01J 2219/00605* (2013.01); *B01J 2219/00623* (2013.01); *B01J 2219/00659* (2013.01); *B01J 2219/00698* (2013.01)

(58) Field of Classification Search
CPC ............ G01R 31/2886; G01R 31/2887; G01R 31/2889; G01N 33/5438; G01N 27/3271; B05C 11/1039; B05C 5/0212; B05C 5/02
USPC .............................................. 438/14, 15, 17
See application file for complete search history.

(56) References Cited

U.S. PATENT DOCUMENTS

| 5,384,028 A * | 1/1995 | Ito ........................ A61B 5/1486 |
| | | 204/403.11 |
| 6,181,145 B1 * | 1/2001 | Tomita ................. G01R 1/0735 |
| | | 324/750.03 |

(Continued)

*Primary Examiner* — Kevin M Picardat
(74) *Attorney, Agent, or Firm* — Eschweiler & Potashnik, LLC

(57) ABSTRACT

The present disclosure relates to a micro-fluidic probe card that deposits a fluidic chemical onto a substrate with a minimal amount of fluidic chemical waste, and an associated method of operation. In some embodiments, the micro-fluidic probe card has a probe card body with a first side and a second side. A sealant element, which contacts a substrate, is connected to the second side of the probe card body in a manner that forms a cavity within an interior of the sealant element. A fluid inlet, which provides a fluid from a processing tool to the cavity, is a first conduit extending between the first side and the second side of the probe card body. A fluid outlet, which removes the fluid from the cavity, is a second conduit extending between the first side and the second side of the probe card body.

20 Claims, 7 Drawing Sheets

(51) Int. Cl.
  B05C 11/10 (2006.01)
  G01R 31/28 (2006.01)
  G01R 1/067 (2006.01)
  G01N 27/414 (2006.01)
  B05D 1/18 (2006.01)
  B05D 5/04 (2006.01)

(56) References Cited

U.S. PATENT DOCUMENTS

| | | | | |
|---|---|---|---|---|
| 6,468,098 | B1* | 10/2002 | Eldridge | G01R 1/0735 439/197 |
| 2005/0151549 | A1* | 7/2005 | Okumura | G01R 31/2898 324/750.03 |
| 2006/0169045 | A1* | 8/2006 | Shinohara | G01N 29/036 73/580 |
| 2009/0000947 | A1* | 1/2009 | Akahori | G01N 27/3272 204/403.14 |
| 2009/0155476 | A1* | 6/2009 | Francis | B05C 3/20 427/421.1 |
| 2010/0181211 | A1* | 7/2010 | Krejci | G01N 27/26 205/792 |
| 2010/0233824 | A1* | 9/2010 | Verhoeckx | B01L 3/502715 436/501 |
| 2011/0262307 | A1* | 10/2011 | Packirisamy | G01N 21/05 422/82.08 |
| 2012/0194213 | A1* | 8/2012 | Komatsu | G01R 31/2887 324/756.03 |
| 2014/0011707 | A1* | 1/2014 | Ye | B01L 3/5027 506/16 |
| 2014/0030799 | A1* | 1/2014 | Yu | G01N 15/1056 435/287.2 |
| 2014/0134748 | A1* | 5/2014 | Liu | B01L 3/502707 436/150 |

* cited by examiner

FLUID DEPOSITION APPARTUS AND METHOD

The deposition of fluidic chemicals onto a substrate is a commonly performed operation during the fabrication of integrated chips. This is because the deposition of a fluidic chemical onto a substrate forms a layer of the chemical that changes the surface properties of the substrate.

For example, in recent years the semiconductor industry has developed bio-chips configured to detect the presence of certain biomarkers in a patient's blood stream. One common form of bio-chip operates to attract target biomarkers within a medium to the channel region of a semiconductor device by using pre-attached capture molecules, which are deposited onto a channel region as a fluidic chemical. Once deposited onto the channel region, the pre-attached capture molecules will attract target biomarkers that produce a change in the electric field around the channel region. Since current flow of the channel region varies with the number of charged target molecules, monitoring this conductance provides an accurate indication of the level of the specific functionalized biomarker.

DETAILED DESCRIPTION

Figure 1A:
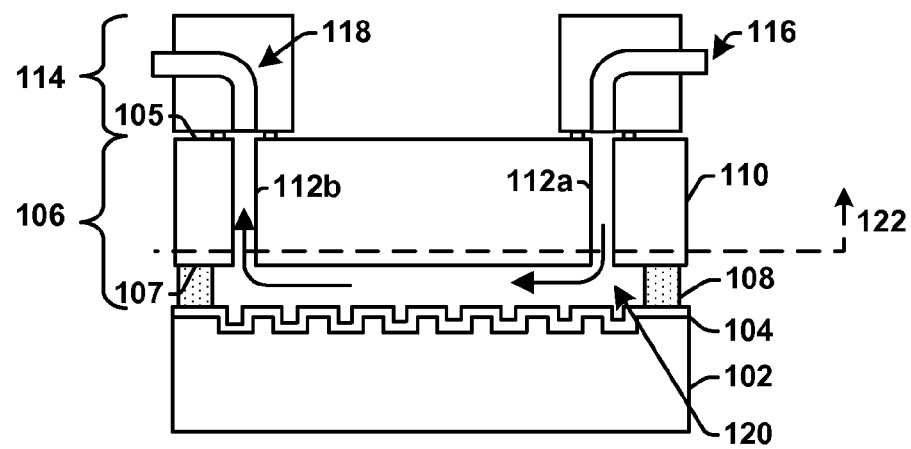
FIGS. 1A-1B illustrate some embodiments of a micro-fluidic probe card configured to deposit a fluid onto a substrate.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one skilled in the art, that one or more aspects described herein may be practiced with a lesser degree of these specific details. In other instances, known structures and devices are shown in block diagram form to facilitate understanding.

Fluidic chemicals may be deposited onto a substrate by a spin coating process or by dunking the substrate into a chemical bath. Spin coating processes are performed by depositing a chemical onto a center of a substrate and then rotating the substrate at a high speed to spread the chemical over the substrate. While spin coating effectively forms a thin layer of the fluidic chemical on a substrate, it provides for both a low rate of chemical reaction and a low rate of chemical recycling. Dunking a substrate into a chemical bath also effectively forms a thin layer of the fluidic chemical on a substrate, but uses a large quantity of the fluidic chemical to immerse entire wafers and can lead to contamination of the fluidic chemical. Given the high cost of chemicals used in some biosensors, the large amount of chemical waste in spin on processes and dunking processes can significantly drive up manufacturing costs.

Accordingly, the present disclosure relates to a micro-fluidic probe card configured to deposit a fluidic chemical onto a substrate with a minimal amount of fluidic chemical waste, and an associated method of operation. In some embodiments, the micro-fluidic probe card comprises a probe card body having a first side and a second side. A sealant element, configured to contact a substrate, is connected to the second side of the probe card body in a manner that forms a cavity within an interior of the sealant element. A fluid inlet, configured to provide a fluid from a processing tool to the cavity, comprises a first conduit extending between the first side and the second side of the probe card body. A fluid outlet, configured to remove the fluid from the cavity, comprises a second conduit extending between the first side and the second side of the probe card body. By providing the fluid to the cavity that abuts a substrate, the fluid can be deposited onto the substrate with a minimal chemical waste.

FIG. 1A illustrates a cross-sectional view 100 of some embodiments of a micro-fluidic probe card 106 configured to deposit a fluid (e.g., a fluidic chemical) onto a substrate 102.

The micro-fluidic probe card 106 comprises a probe card body 110 connected to a sealant element 108. The probe card body 110 has a first side 105 and a second side 107, opposite the first side 105. The first side 105 is in communication with a processing tool 114. The second side 107 is in communication with an exposure chamber 120 configured to abut a substrate 102. In some embodiments, the substrate 102 may comprise a MEMs (microelectromechanical system) biosensor having one or more devices 104 (e.g., field effect transistors) located along the surface of the substrate 102, which are configured to detect the presence of a bio-marker or byproduct of a biological reaction within a fluid provided to the exposure chamber 120.

The probe card body 110 comprises a fluid inlet 112a and a fluid outlet 112b. The fluid inlet 112a comprises a first conduit that extends between the first side 105 of the probe card body 110 and the second side 107 of the probe card body 110. The fluid inlet 112a is configured to provide fluid from the processing tool 114 (e.g., from processing tool inlet 116) to the exposure chamber 120. The fluid outlet 112b comprises a second conduit that extends between the first side 105 of the probe card body 110 and the second side 107 of the probe card body 110. The fluid outlet 112b is configured to remove the fluid from the exposure chamber 120 (e.g., to processing tool outlet 118).

The sealant element 108 is disposed onto the second side 107 of the probe card body 110 at a position that contacts the substrate 102. The sealant element 108 comprises a hollow interior, in communication with the fluid inlet 112a and the fluid outlet 112b. The hollow interior of the sealant element 108 forms a cavity in a backside of the micro-fluidic probe card 106, such that the sealant element 108 forms sidewalls of the exposure chamber 120. The sealant element 108 comprises a material that prevents leakage of the fluid from the exposure chamber 120. In some embodiments, the sealant element 108 may comprise a material that is selected to provide for a high resistance to a fluidic chemical. In some embodiments, the sealant element 108 may comprise elastic polymer contacts, such as PDMS (Polydimethylsiloxane), EPDM (ethylene propylene diene monomer), FKM (fluoroelastomer), FFKM (perfluoro-elastomer), or PTFE (Polytetrafluoroethylene), for example.

Figure 1B:

FIG. 1B illustrates a top view 124 of the micro-fluidic probe card of FIG. 1A (shown along cross-sectional line 122 in FIG. 1A). As shown in top view 124, the fluid inlet 112a and the fluid outlet 112b are located at opposite ends of the micro-fluidic probe card 106. By placing the fluid inlet 112a and the fluid outlet 112b at opposing ends, the fluid moves over the surface of the substrate 102.

Figure 2:
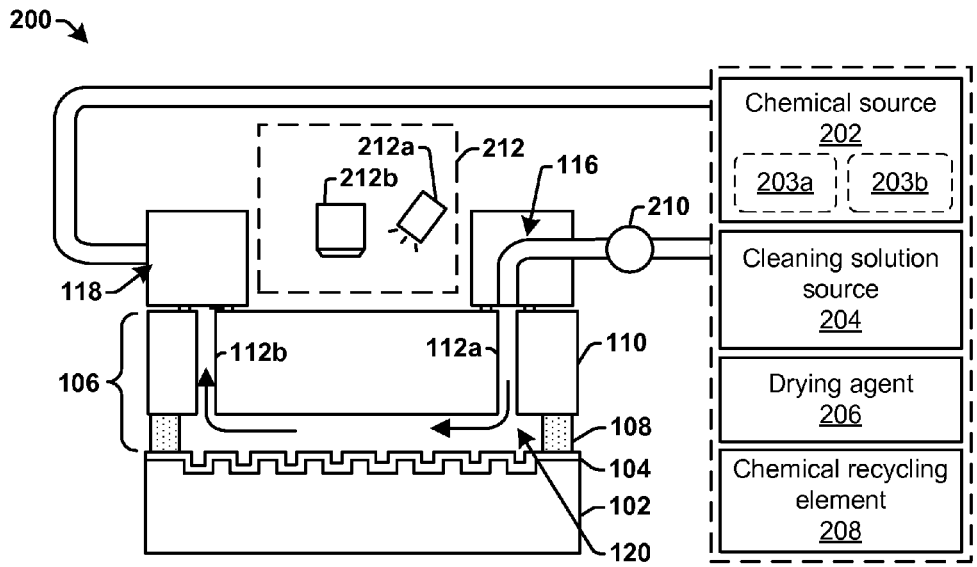
FIG. 2 illustrates a block diagram of some additional embodiments of a micro-fluidic probe card configured to deposit a fluid onto a substrate.

FIG. 2 illustrates a block diagram of some additional embodiments of a micro-fluidic system 200 comprising a micro-fluidic probe card 106 configured to deposit a fluid onto a substrate 102.

The micro-fluidic probe card 106 is connected to the substrate 102. In various embodiments, the substrate 102 may comprise a semiconductor substrate (e.g., a silicon substrate, a germanium substrate, etc.), a quartz substrate, a glass substrate, or a substrate comprising a similar material. In some embodiments, the substrate 102 may comprise a MEMs wafer having one or more MEMs (microelectromechanical system) devices. For example, in some embodiments, the substrate 102 may comprise a MEMs sensor configured to detect the presence of a biomarker or a byproduct of a biological reaction within a fluid.

The micro-fluidic probe card 106 comprises a fluid inlet 112a that is selectively coupled to a chemical source 202, a cleaning solution source 204, a drying agent source 206, or a chemical recycling element 208. In some embodiments, the micro-fluidic probe card 106 is selectively coupled to the chemical source 202, the cleaning solution source 204, the drying agent source 206, or the chemical recycling element 208 by way of a valve 210.

The chemical source 202 is configured to selectively provide one or more fluidic chemicals (e.g., a hydrogel base, a primer, and/or a bio-entity) to the exposure chamber 120. The chemical source 202 may comprise one or more chemical tanks, 203a and 203b, respectively configured to contain a chemical. For example, the first chemical tank 203a may comprise a first chemical, and the second chemical tank 203b may comprise a second chemical. It will be appreciated that the size of the one or more chemical tanks, 203a and 203b, may vary depending upon the size of the micro-fluidic probe card 106. For example, if the micro-fluidic probe card 106 is configured to provide the chemical(s) to a local region of the substrate 102, the tanks, 203a and 203b, may be smaller than if the micro-fluidic probe card 106 is configured to globally provide the chemical(s) to substrate 102.

In some embodiments, the chemical source 202 is configured to provide different fluidic chemicals to the exposure chamber 120 at different times. For example, the chemical source 202 may be configured to provide a first chemical to the exposure chamber 120 at a first time and to provide a second chemical to the exposure chamber 120 at a subsequent, second time. In some embodiments, the chemical source 202 may be configured to provide an adhesive promoter comprising an aminosilane base which can functionalize the substrate surface (e.g., 3-Aminopropyl)triethoxysilane (APTES)). In other embodiments, the chemical source 202 may be configured to provide a medium having functional groups which can react with adhesive promoter and primers (e.g., a functional hydrogel). In yet other embodiments, the chemical source 202 may be configured to provide bio-entities (e.g., DNA, RNA, and/or proteins) attached to primers which attached to a hydrogel's functional groups.

The cleaning solution source 204 is configured to selectively provide a cleaning solution to the exposure chamber 120. The cleaning solution is configured to remove a residue of a fluidic chemical from the exposure chamber 120. In various embodiments, the cleaning solution may comprise one or more of toluene, alcohol, and/or de-ionized water. In some embodiments, the cleaning solution source 204 may be configured to output a first cleaning solution at a first time followed by a second cleaning solution at a second time. For example, in some embodiments, the cleaning solution source 204 is configured to provide the exposure chamber with de-ionized water and isopropyl alcohol.

The drying agent source 206 is configured to selectively provide a drying agent to the exposure chamber 120. The drying agent is configured to dry the substrate 102. In some embodiments, the drying agent source 206 is configured to provide a nitrogen gas ($N_2$) to the substrate 102. The nitrogen gas purges the substrate 102 to remove fluid from the surface of the substrate 102.

The chemical recycling element 208 is configured to receive the fluidic chemicals removed from the exposure chamber 120 (via fluid outlet 112b) and to recycle the removed fluidic chemicals by providing the removed chemicals back to the fluid inlet 112a. Since the fluidic chemical is provided to the top surface of the substrate 102, the fluidic chemical is not highly contaminated and therefore can be reused during sequent depositions of the fluidic chemical.

In some embodiments, the chemical recycling element 208 comprises an analysis element configured to determine a level of contamination in the removed fluidic chemical and to selectively provide the removed fluidic chemical back to the exposure chamber 120 depending upon the measured level of contamination. For example, if the level of contamination is below a predetermined threshold, the chemical recycling element 208 will provide the removed fluidic chemicals back to the exposure chamber 120 by way of the fluid inlet 112a, while if the level of contamination is above the predetermined threshold the chemical recycling element 208 will not provide the removed fluidic chemicals back to the exposure chamber 120.

In some embodiments, a performance monitoring element 212 is configured to determine if a fluidic chemical has been applied to the substrate 102. In some embodiments, the performance monitoring element 212 is configured to perform an in-situ monitoring process that inspects the chemical deposition (i.e., that inspects the chemical deposition without removing the micro-fluidic probe card 106 from the substrate 102).

In some embodiments, the micro-fluidic probe card 106 comprises a transparent surface positioned between the performance monitoring element 212 and the substrate 102. In such embodiments, the performance monitoring element 212 may comprise a light source 212a and a fluorescence monitor 212b. The light source 212a is configured to provide a light (i.e., electromagnetic radiation) to the surface of the substrate 102. The fluorescence monitor 212b is configured to measure a fluorescence response (e.g., a light radiation level) of a fluidic chemical deposited onto the substrate 102. If the fluorescence monitor 212b receives a fluorescence response, it indicates that the fluidic chemical has been applied to the surface of the substrate 102. If the fluorescence monitor 212b does not receive a fluorescence response, it indicates that the fluidic chemical has not been applied to the surface of the substrate 102.

Figure 3A:
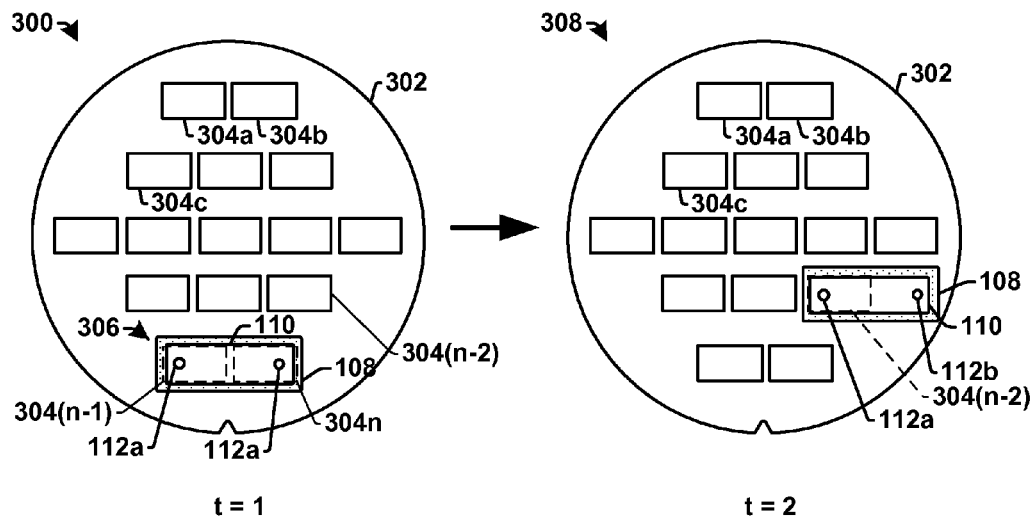
FIGS. 3A-3B illustrate top views of some embodiments of a micro-fluidic probe card configured to deposit a fluid onto a substrate.
Figure 3B:
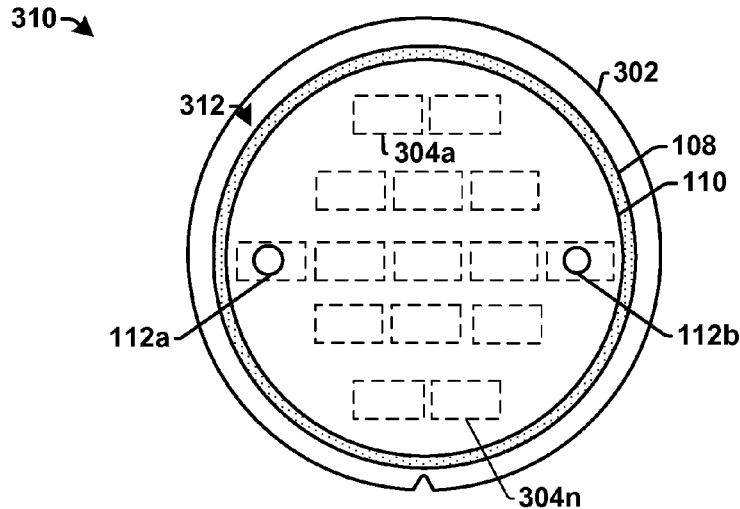

FIGS. 3A-3B illustrate top views of some embodiments of micro-fluidic probe cards, 306 and 312, configured to deposit a fluid onto a substrate 302.

FIG. 3A illustrates top views, 300 and 308, of a micro-fluidic probe card 306 configured to provide a fluid to local region of a substrate 302 comprising a plurality of sub-regions 304a-304n. In some embodiments, the plurality of sub-regions 304a-304n may respectively comprise a multi-device pattern, having a plurality of devices (e.g., MEMs sensors, field effect transistors, etc.) located within a region of the substrate 302.

The micro-fluidic probe card 306 has a size that is comparable to the size of less than the plurality of sub-regions 304a-304n. For example, the micro-fluidic probe card 306 may have a rectangular shape that has a size substantially equal to the size of two of the plurality of sub-regions 304a, 304b, . . . , or 304n. In some embodiments, the micro-fluidic probe card 306 may have a length having a size in a range of between approximately 10 nanometers and approximately 200 nanometers.

The micro-fluidic probe card 306 is configured to provide a fluid (e.g., a fluidic chemical) to one of the plurality of sub-regions 304a, 304b, . . . , or 304n at a given time. By moving the micro-fluidic probe card 306 between the various sub-regions 304a, 304b, . . . , or 304n of the substrate 302, the fluid is provided to the substrate 302 over a plurality of time periods.

For example, at a first time, t=1 (illustrated in cross-sectional view 300), the micro-fluidic probe card 306 may be configured to provide a fluid (e.g., a fluidic chemical) to sub-regions 304(n−1) and 304n of the substrate 302. At a second time, t=2 (illustrated in cross-sectional view 308), the micro-fluidic probe card 306 may be configured to provide a fluid (e.g., a fluidic chemical) to sub-region 304(n−2) of the substrate 302.

FIG. 3B illustrates a top view of a micro-fluidic probe card 312 configured to provide a fluid to a global region of a substrate 302 comprising a plurality of sub-regions 304a-304n. In some embodiments, the plurality of sub-regions 304a-304n may respectively comprise a multi-device pattern having a plurality of MEMs devices (e.g., MEMs sensors).

The micro-fluidic probe card 312 is configured to provide a fluid (e.g., a fluidic chemical) to a substantial area of the semiconductor wafer 310 at a given time. In some embodiments, the micro-fluidic probe card 312 has a size that is comparable to a size of the semiconductor wafer 310 so as to provide the fluid to the plurality of sub-regions 304a-304n at a same time. For example, the micro-fluidic probe card 312 may have a circular shape with a diameter that has a size in a range of between approximately 200 nanometers and approximately 300 nanometers.

Figure 4:
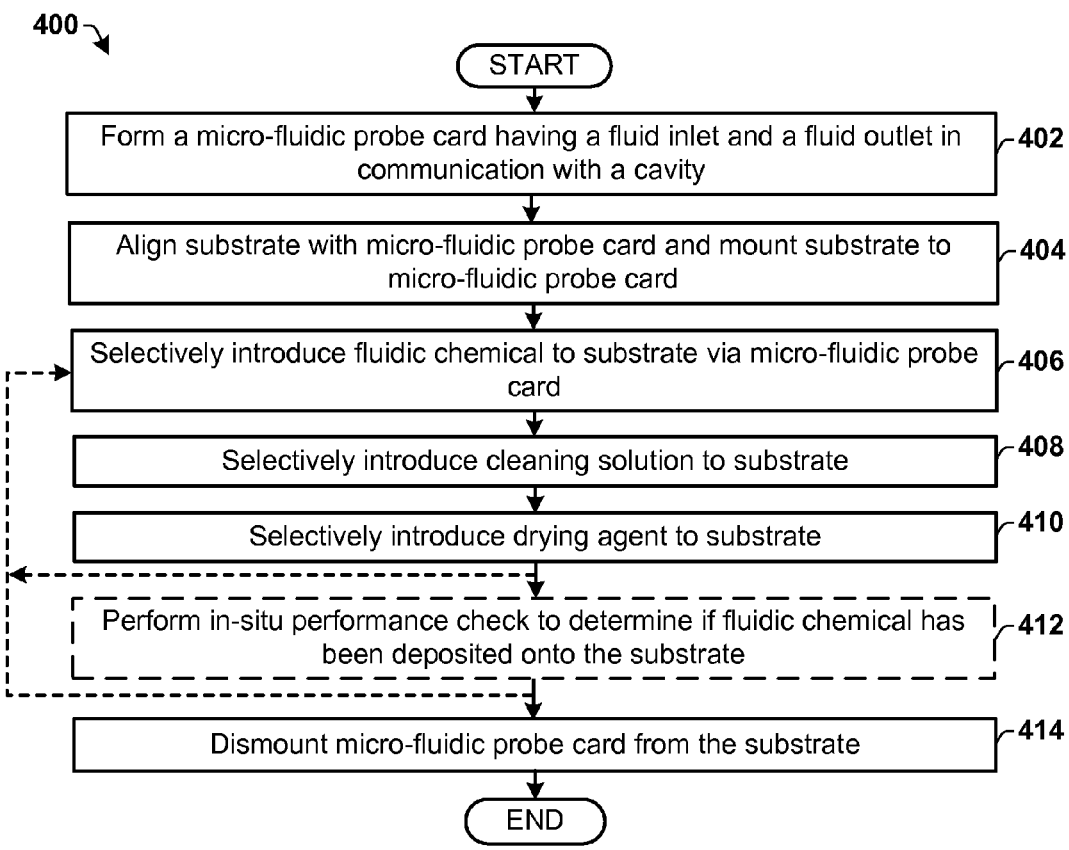
FIG. 4 illustrates a flow diagram of some embodiments of a method of depositing a fluid onto a substrate.

FIG. 4 illustrates a flow diagram of some embodiments of a method 400 of depositing a fluid (e.g., a fluidic chemical) onto a substrate (e.g., a MEMs biosensor).

While disclosed method 400 is illustrated and described below as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 402, a micro-fluidic probe card is formed. The micro-fluidic probe card comprises a cavity configured to form an exposure chamber that abuts a substrate to be coated with the fluid. The micro-fluidic probe card has a fluid inlet configured to provide fluids (e.g., fluidic chemicals) to the exposure chamber and a fluid outlet configured to remove fluids (e.g., fluidic chemicals) from the exposure chamber.

At 404, a substrate is aligned with and mounted to the micro-fluidic probe card. Mounting the substrate to the micro-fluidic probe card results in the formation of hermetically sealed exposure chamber that abuts the substrate. The exposure chamber is configured to expose a surface of the substrate to a fluid (e.g., a fluidic chemical) provided from a processing tool.

At 406, a fluidic chemical is selectively introduced to the substrate via the micro-fluidic probe card. The fluidic chemical is selectively introduced to the substrate by providing the fluidic chemical to the exposure chamber that abuts the substrate.

At 408, a cleaning solution is selectively introduced to the substrate via the micro-fluidic probe card. The cleaning solution is selectively introduced to the substrate by providing the cleaning solution to the exposure chamber that abuts the substrate. The cleaning solution is configured to remove a residue of the fluidic chemical from the exposure chamber.

At 410, a drying agent is selectively introduced to the substrate via the micro-fluidic probe card. The drying agent is selectively introduced to the substrate by providing the drying agent to the exposure chamber that abuts the substrate.

In some embodiments, acts 406-410 may be iteratively repeated to deposit a plurality of fluidic chemicals onto the substrate. For example, acts 406-410 may be performed a first time to deposit a first fluidic chemical onto the substrate, and acts 406-410 may be performed a second time to deposit a second fluidic chemical onto the substrate.

At 412, an in-situ performance check may be performed to determine if a fluidic chemical has been deposited onto the substrate, in some embodiments. The in-situ performance check determines if the fluidic chemical has been deposited onto the substrate without dismounting the micro-fluidic probe card from the substrate.

In some embodiments, if the performance check indicates that the fluidic chemical has not been deposited onto the substrate acts 406-412 may be repeated until the performance check indicates that the fluidic chemical has been deposited onto the substrate.

At 414, the micro-fluidic probe card is dismounted from the substrate. After the micro-fluidic probe card is dismounted, the substrate may be removed from the processing tool and attached to another substrate or the micro-fluidic probe card may be moved to a next device area on the same substrate.

FIGS. 5-10 illustrate some embodiments of a substrate upon which a method of depositing a fluid on a substrate is performed. Although FIGS. 5-10 are described in relation to method 400, it will be appreciated that the structures disclosed in FIGS. 5-10 are not limited to such a method, but instead may stand alone as a structure.

Figure 5:
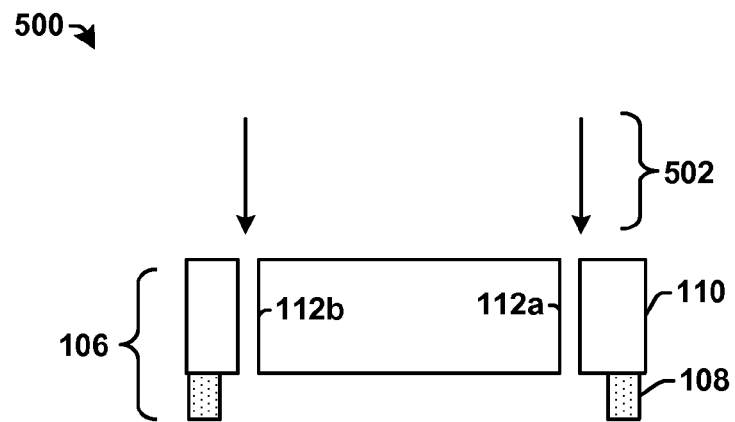
FIGS. 5-10 illustrate some embodiments of a substrate upon which a method of depositing a fluid onto a substrate is performed.

FIG. 5 illustrates some embodiments of a cross-sectional view 500 corresponding to act 402. As shown in cross-sectional view 500, a micro-fluidic probe card 106 is formed. The micro-fluidic probe card 106 is formed by forming a fluid inlet 112a and a fluid outlet 112b within a probe card body 110. In some embodiments, the fluid inlet 112a and the fluid outlet 112b are formed using an etchant 502. In various embodiments, the etchant 502 may comprise laser drilling or sand blasting. The probe card body 110 is then attached to a sealant element 108.

Figure 6A:
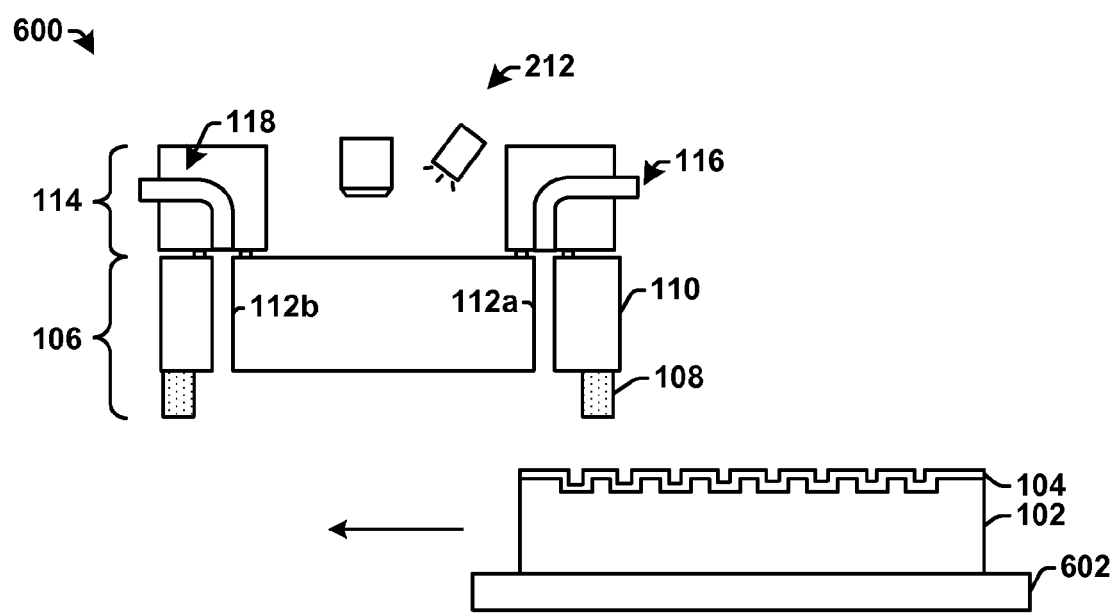
Figure 6B:
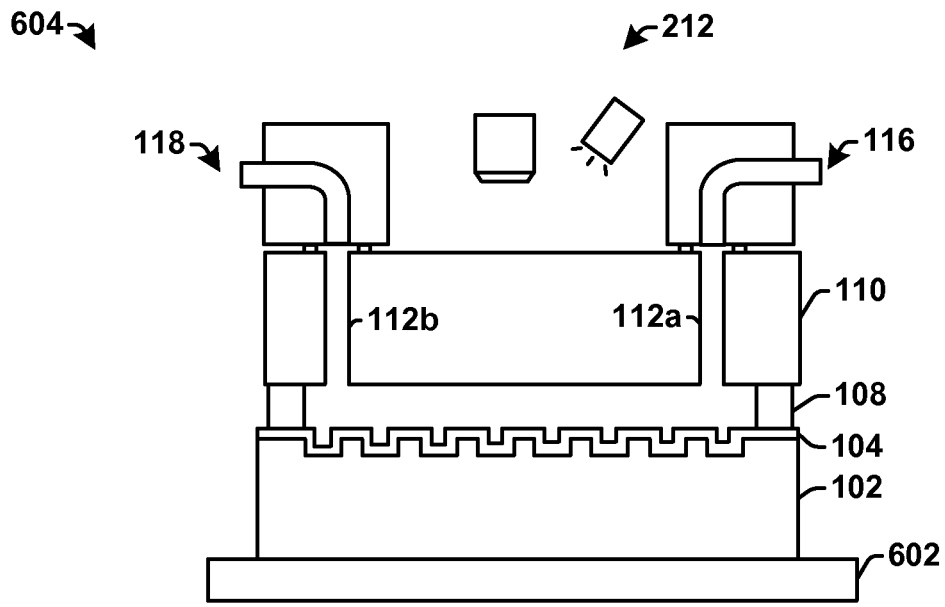

FIGS. 6A-6B illustrate some embodiments of cross-sectional views, 600 and 604, corresponding to act 404.

As shown in cross-sectional view 600, a substrate 102 is aligned with the micro-fluidic probe card 106. In some embodiments, the substrate 102 may be located on a mobile stage 602 associated with a processing tool 114. The mobile stage 602 is configured to move the substrate 102 into a position that is aligned with the micro-fluidic probe card 106.

In various embodiments, the substrate 102 may comprise a semiconductor wafer or a portion of a semiconductor wafer. In some embodiments, the substrate 102 may comprise an epitaxial layer disposed above a semiconductor wafer. In other embodiments, the substrate 102 may comprise quartz, silicon, glass, etc. In some embodiments, the substrate 102 may comprise a MEMs wafer having one or more MEMs (microelectromechanical system) devices. For example, the substrate may comprise a MEMs (microelectromechanical system) bio-sensor having one or more devices 104 (e.g., field effect transistors) located along the surface of the substrate 102, which are configured to detect the presence of a bio-marker or byproduct of a biological reaction within a fluid.

As shown in cross-sectional view 604, after the substrate 102 has been aligned with the micro-fluidic probe card 106, the substrate 102 is brought into physical contact with the sealant element 108 of the micro-fluidic probe card 106 to form a hermetically sealed exposure chamber 120. The hermetically sealed exposure chamber 120 abuts the substrate 102 along a side of the substrate 102 that is to be exposed to a fluid (e.g., fluidic chemical). The hermetically sealed exposure chamber 120 is connected to the fluid inlet 112a, which is configured to provide a fluid to the exposure chamber 120, and to the fluid outlet 112b, which is configured to remove the fluid from the exposure chamber 120.

Figure 7:
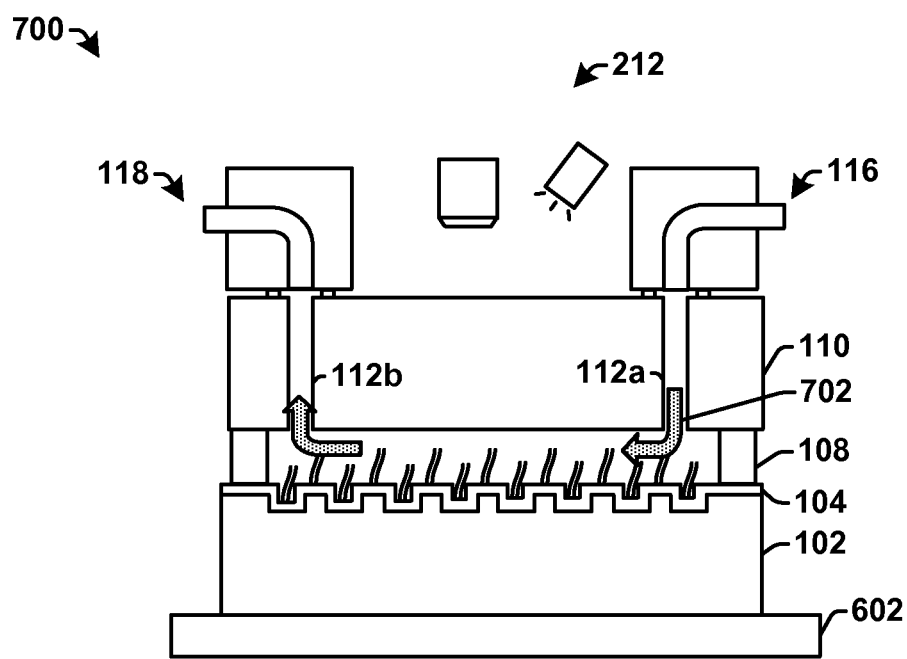

FIG. 7 illustrates some embodiments of a cross-sectional view 700 corresponding to act 406. As shown in cross-sectional view 700, a fluidic chemical 702 is introduced to the substrate 102 via the micro-fluidic probe card 106. The fluidic chemical 702 is introduced to the substrate 102 by providing the fluidic chemical 702 to the exposure chamber 120 by way of the fluid inlet 112a. In some embodiments, the fluidic chemical 702 may comprise an adhesive promoter comprising an aminosilane base which can functionalize the substrate surface (e.g., 3-Aminopropyl)triethoxysilane (APTES)). In other embodiments, the fluidic chemical 702 may comprise a medium having functional groups which can react with adhesive promoter and primers (e.g., a functional hydrogel). In yet other embodiments, the fluidic chemical 702 may comprise bio-entities (e.g., DNA, RNA, and/or proteins) attached to primers which attached to a hydrogel's functional groups.

Figure 8:
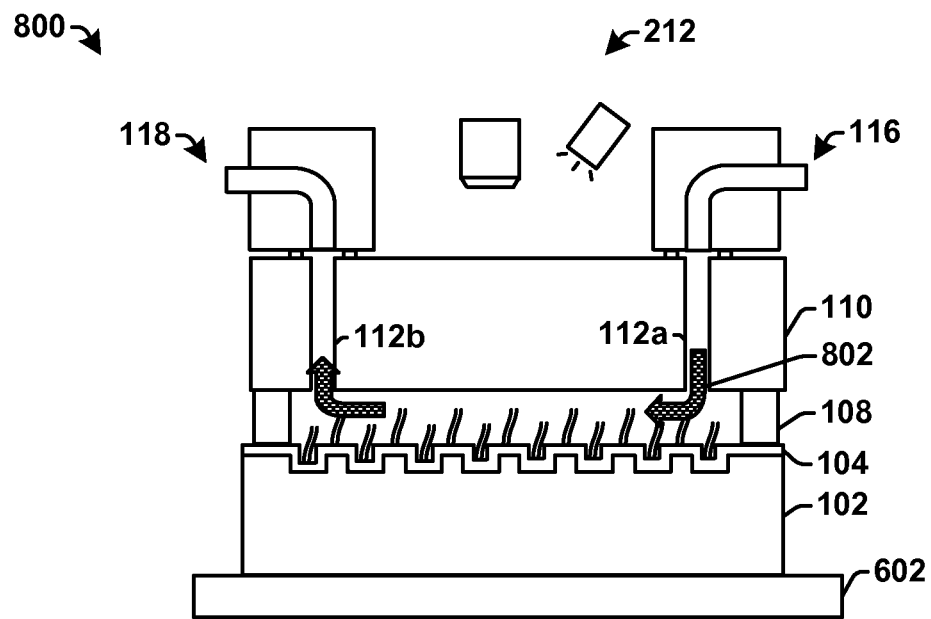

FIG. 8 illustrates some embodiments of a cross-sectional view 800 corresponding to acts 408-410. As shown in cross-sectional view 800, a cleaning solution 802 is introduced to the substrate 102 via the micro-fluidic probe card 106. The cleaning solution 802 is introduced to the substrate 102 by providing the cleaning solution 802 to the exposure chamber 120 by way of the fluid inlet 112a. In some embodiments, the cleaning solution 802 may comprise de-ionized water and/or an isopropyl alcohol flush.

In some embodiments, a drying agent may also be introduced to the substrate 102 via the micro-fluidic probe card 106. The drying agent may be introduced to the substrate 102 by providing the drying agent to the exposure chamber 120 by way of the fluid inlet 112a. In some embodiments, the drying agent may comprise a nitrogen gas ($N^2$) purge.

It will be appreciated that the micro-fluidic probe card may be used to introduce a number of different fluidic chemicals to the substrate 102 by repeating acts 406-410. For example, a first chemical may be introduced to the substrate 102 (at act 406) and subsequently flushed (at act 408). After the first chemical is flushed, a second chemical may be introduced to the substrate 102 (at act 406) and subsequently flushed (at act 408).

Figure 9:
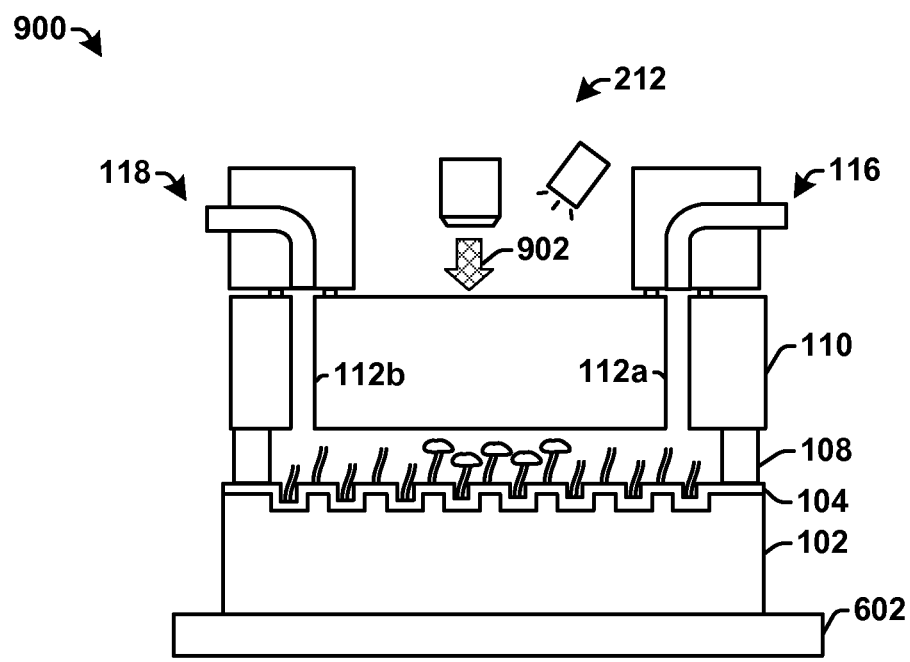

FIG. 9 illustrates some embodiments of a cross-sectional view 900 corresponding to act 412. As shown in cross-sectional view 900, an in-situ performance check is performed to determine if a fluidic chemical has been deposited onto the substrate. In some embodiments, the performance check is performed by operating a performance monitoring element 212 to provide a light 902 to a surface of the substrate 102 and then monitoring the surface to measure a fluorescence response. If a fluorescence response is detected, the fluidic chemical was properly deposited onto the substrate 102. If a fluorescence response is not detected, the fluidic chemical was not properly deposited onto the substrate 102.

Figure 10:
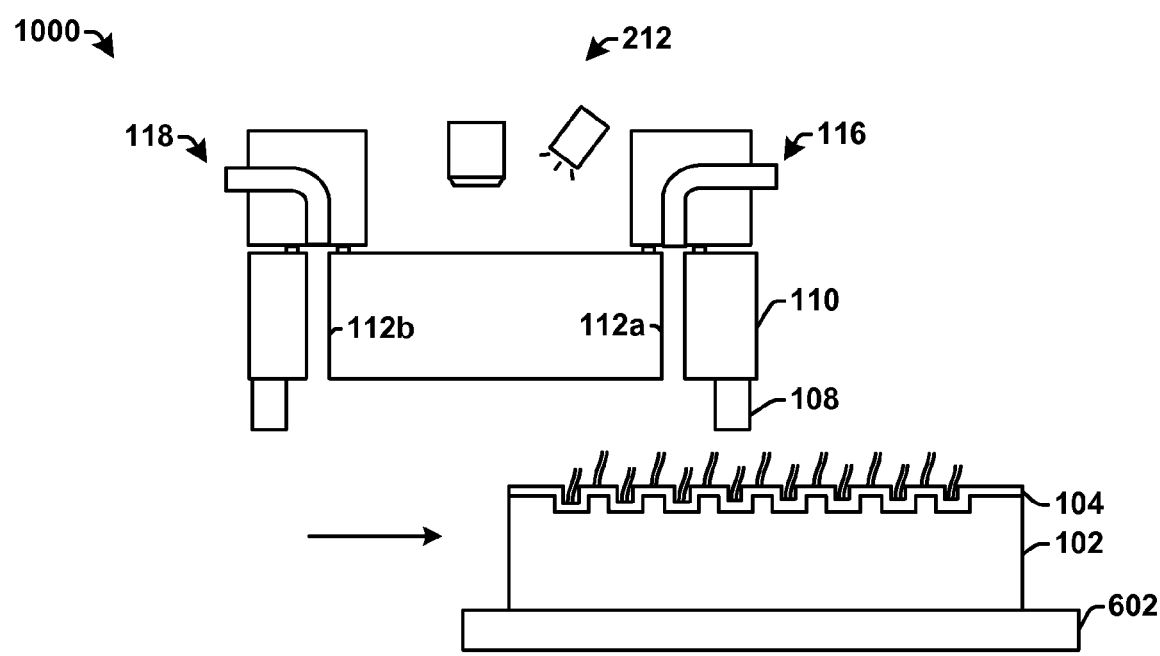

FIG. 10 illustrates some embodiments of a cross-sectional view 1000 corresponding to act 414. As shown in cross-sectional view 1000, the micro-fluidic probe card 106 is dismounted from the substrate 102 and the substrate 102 is removed from the processing tool 114. In some embodiments, where the substrate 102 is located on a mobile stage 602 of a processing tool 114, the mobile stage 602 is configured to move the substrate 102 into a position away from the micro-fluidic probe card 106.

It will be appreciated that while reference is made throughout this document to exemplary structures in discussing aspects of methodologies described herein (e.g., the structure presented in FIGS. 5-10, while discussing the methodology set forth in FIG. 4), that those methodologies are not to be limited by the corresponding structures presented. Rather, the methodologies (and structures) are to be considered independent of one another and able to stand alone and be practiced without regard to any of the particular aspects depicted in the Figs. Additionally, layers described herein, can be formed in any suitable manner, such as with spin on, sputtering, growth and/or deposition techniques, etc.

Also, equivalent alterations and/or modifications may occur to those skilled in the art based upon a reading and/or understanding of the specification and annexed drawings. The disclosure herein includes all such modifications and alterations and is generally not intended to be limited thereby. For example, although the figures provided herein, are illustrated and described to have a particular doping type, it will be appreciated that alternative doping types may be utilized as will be appreciated by one of ordinary skill in the art.

In addition, while a particular feature or aspect may have been disclosed with respect to only one of several implementations, such feature or aspect may be combined with one or more other features and/or aspects of other implementations as may be desired. Furthermore, to the extent that the terms "includes", "having", "has", "with", and/or variants thereof are used herein, such terms are intended to be inclusive in meaning—like "comprising." Also, "exemplary" is merely meant to mean an example, rather than the best. It is also to be appreciated that features, layers and/or elements depicted herein are illustrated with particular dimensions and/or orientations relative to one another for purposes of simplicity and ease of understanding, and that the actual dimensions and/or orientations may differ substantially from that illustrated herein.

The present disclosure relates to a micro-fluidic probe card configured to deposit a fluidic chemical onto a substrate with a minimal amount of fluidic chemical waste, and an associated method of operation In some embodiments, the present disclosure relates to a micro-fluidic probe card. The micro-fluidic probe card comprises a probe card body having a first side and a second side. The micro-fluidic probe card further comprises a sealant element connected to the second side of the probe card body in a manner that forms a cavity within a hollow interior of the sealant element. The micro-fluidic probe card further comprises a fluid inlet comprising a first conduit extending between the first side and the second side, wherein the fluid inlet is configured to provide a fluid from a processing tool to the cavity, and a fluid outlet comprising a second conduit extending between the first side and the second side, wherein the fluid outlet is configured to remove the fluid from the cavity.

In other embodiments, the present disclosure relates to a micro-fluidic probe card. The micro-fluidic probe card comprises a fluid inlet having a first conduit extending between a first side of a micro-fluidic probe card and a second side of the micro-fluidic probe card, wherein the fluid inlet is configured to provide a fluidic chemical from a processing tool to an exposure chamber on the second side of the micro-fluidic probe card. The micro-fluidic probe card further comprises a fluid outlet having a second conduit extending between the first side and the second side, wherein the fluid outlet is configured to remove the fluidic chemical from the exposure chamber. The micro-fluidic probe card further comprises a sealant element configured to abut a substrate, wherein the sealant element is connected to the second side of the micro-fluidic probe card at a position that forms sidewalls of the exposure chamber.

In yet other embodiments, the present disclosure relates to a method of depositing a fluid onto a substrate. The method comprises forming a micro-fluidic probe card having a fluid inlet and a fluid outlet in communication with a exposure chamber and aligning a substrate with the micro-fluidic probe card. The method further comprises mounting the substrate to the micro-fluidic probe card at a position abutting the exposure chamber. The method further comprises selectively introducing a first fluidic chemical to the substrate via the fluid inlet of the micro-fluidic probe card. The method further comprises dismounting the micro-fluidic probe card from the substrate.

What is claimed is:

1. A micro-fluidic probe card, comprising:
a probe card body having a first side and a second side;
a sealant element connected to the second side of the probe card body in a manner that forms a cavity within a hollow interior of the sealant element, wherein the cavity is configured to contact a substrate comprising one or more bio-sensors;
a fluid inlet comprising a first conduit extending between the first side and the second side, wherein the fluid inlet is configured to provide a fluid from a processing tool to the cavity;
a fluid outlet comprising a second conduit extending between the first side and the second side, wherein the fluid outlet is configured to remove the fluid from the cavity;
a performance monitoring element configured to perform an in-situ monitoring process to determine if the fluid has been applied to the substrate, wherein the performance monitoring element comprises an electromagnetic radiation source configured to provide electromagnetic radiation to the fluid and a fluorescence monitor configured to measure a fluorescence response of the fluid; and
wherein the probe card body comprises a transparent surface positioned between the performance monitoring element and the substrate.

2. The micro-fluidic probe card of claim 1, further comprising:
a chemical source configured to selectively provide one or more fluidic chemicals to the cavity via the fluid inlet.

3. The micro-fluidic probe card of claim 1, further comprising:
a chemical recycling element configured to receive fluidic chemicals removed from the cavity via the fluid outlet and to provide the removed fluidic chemicals to the cavity via the fluid inlet.

4. The micro-fluidic probe card of claim 1, further comprising:
a cleaning solution source configured to selectively provide a cleaning solution to the cavity via the fluid inlet.

5. The micro-fluidic probe card of claim 1, further comprising:
a drying agent source configured to selectively provide a drying agent to the cavity via the fluid inlet.

6. The micro-fluidic probe card of claim 1,
wherein the substrate configured to contact with the cavity comprises a plurality of sub-regions respectively comprising one or more devices; and
wherein the cavity is defined by sidewalls of the sealant element, which are configured to continuously surround a number of sub-regions less than the plurality of sub-regions at a given time.

7. The micro-fluidic probe card of claim 1,
wherein the substrate configured to contact with the cavity comprises a plurality of sub-regions; and
wherein the micro-fluidic probe card is configured to provide the fluid to the plurality of sub-regions at a same time.

8. The micro-fluidic probe card of claim 1, wherein the sealant element is configured to contact an upper surface of the substrate, so that the upper surface of the substrate forms a lower surface of the cavity.

9. The micro-fluidic probe card of claim 1, wherein the micro-fluidic probe card comprises a transparent material.

10. The micro-fluidic probe card of claim 1, wherein sidewalls of the probe card body are completely confined between the first side and the second side.

11. The micro-fluidic probe card of claim 1, wherein the sealant element comprises an elastic polymer.

12. The micro-fluidic probe card of claim 1, wherein the sealant element comprises polydimethylsiloxane, ethylene propylene diene monomer, fluoroelastomer, perfluoro-elastomer, or polytetrafluoroethylene.

13. The micro-fluidic probe card of claim 1, wherein the sealant element is arranged completely below the first conduit and the second conduit.

14. A micro-fluidic probe card, comprising:
a fluid inlet comprising a first conduit extending between a first surface of a micro-fluidic probe card and a second surface of the micro-fluidic probe card, wherein the fluid inlet is configured to provide a fluidic chemical from a processing tool to an exposure chamber on the second surface of the micro-fluidic probe card;
a fluid outlet comprising a second conduit extending between the first surface and the second surface, wherein the fluid outlet is configured to remove the fluidic chemical from the exposure chamber;
a sealant element configured to contact a substrate having one or more biosensors, wherein the sealant element is connected to the second surface of the micro-fluidic probe card at a position that forms sidewalls of the exposure chamber;

wherein the fluid inlet and the fluid outlet are defined by sidewalls of the micro-fluidic probe card, which are coupled between the first surface and the second surface;

a performance monitoring element configured to perform an in-situ monitoring process to determine if the fluidic chemical has been applied to the substrate in contact with the exposure chamber;

wherein the micro-fluidic probe card comprises a transparent surface positioned between the performance monitoring element and the substrate; and wherein the performance monitoring element comprises a light source configured to provide a light to the fluidic chemical, and a fluorescence monitor is configured to measure a fluorescence response of the fluidic chemical.

15. The micro-fluidic probe card of claim 14, further comprising:

a chemical recycling element configured to receive the fluidic chemical removed from the exposure chamber via the fluid outlet and to provide the removed fluidic chemical to the exposure chamber via the fluid inlet.

16. The micro-fluidic probe card of claim 14, further comprising:

a drying agent source configured to selectively provide a drying agent to the exposure chamber via the fluid inlet.

17. The micro-fluidic probe card of claim 14, wherein the sealant element comprises an o-ring.

18. The micro-fluidic probe card of claim 14, wherein the sealant element is arranged completely below the sidewalls of the micro-fluidic probe card defining the fluid inlet and the fluid outlet.

19. A micro-fluidic probe card, comprising:

a probe card body having a first side and a second side;

a sealant element connected to the second side of the probe card body in a manner that forms a cavity within a hollow interior of the sealant element, wherein the cavity is configured to contact a substrate comprising one or more bio-sensors;

a fluid inlet comprising a first conduit extending between the first side and the second side, wherein the fluid inlet is configured to provide a fluid from a processing tool to the cavity;

a fluid outlet comprising a second conduit extending between the first side and the second side, wherein the fluid outlet is configured to remove the fluid from the cavity; and a chemical recycling element configured to receive the fluid removed from the cavity via the fluid outlet and to provide the removed fluid to the cavity via the fluid inlet.

20. The micro-fluidic probe card of claim 19, wherein the fluid inlet and the fluid outlet are defined by sidewalls of the probe card body, which are completely confined between the first side and the second side.

* * * * *